United States Patent [19]

Sonnewald

[11] Patent Number: 4,931,450
[45] Date of Patent: Jun. 5, 1990

[54] AMINO ACID DERIVATIVES

[75] Inventor: Ursula Sonnewald, Ballerup, Denmark

[73] Assignee: Novo Industri A/S, Bagsvaerd, Denmark

[21] Appl. No.: 259,235

[22] Filed: Oct. 17, 1988

Related U.S. Application Data

[63] Continuation-in-part of Ser. No. 755, Jan. 6, 1987, abandoned.

[30] Foreign Application Priority Data

Jan. 7, 1986 [DK] Denmark .................................. 51/86
Mar. 3, 1986 [DK] Denmark ................................ 956/86

[51] Int. Cl.$^5$ ..................... A61K 31/44; C07D 401/06
[52] U.S. Cl. .................................... 514/326; 514/332; 514/340; 514/342; 514/343; 514/422; 546/194; 546/208; 546/213; 546/214; 546/261; 546/263; 546/281; 546/283; 546/284; 548/517; 548/524; 548/527
[58] Field of Search ............... 546/194, 208, 213, 214, 546/261, 263, 281, 283, 284; 548/517, 527, 524; 514/326, 332, 340, 342, 343, 422

[56] References Cited

U.S. PATENT DOCUMENTS 4,383,999  5/1983  Bondinell et al. ................... 546/213
4,681,884  7/1987  Grozinger et al. ................. 514/311

OTHER PUBLICATIONS

Younger et al., "Chemical Abstracts", vol. 100, 1984, col. 100:114852t.
Sonnewald, "Chemical Abstracts", vol. 108, 1988, col. 108:167299q.

*Primary Examiner*—Glennon H. Hollrah
*Assistant Examiner*—James H. Turnipseed
*Attorney, Agent, or Firm*—Morris Fidelman; Franklin D. Wolffe

[57] ABSTRACT

Compounds of the Formula I

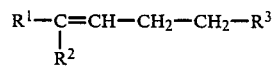

wherein $R^1$ represents phenyl, or phenyl substituted by one, or more substituents selected from the group consisting of halogen, $C_{1-7}$-alkyl, and $C_{1-7}$-alkoxy, $R^2$ represents furanyl, thienyl, pyridyl or pyrrolyl ortho substituted with $C_{1-7}$-alkyl or halogen and wherein $R^3$ represents 3-carboxypiperidin-1-yl, 3-carboxy-1,2,5,6-tetrahydropyridin-1-yl or 3-carboxymethyl-pyrrolidin-1-yl, pharmaceutical compositions containing effective amounts of a compound of formula I and treatment of central nervous system ailments by administering a compound of formula I.

15 Claims, No Drawings

AMINO ACID DERIVATIVES

This application is continuation in part of our patent application Ser. No. 07/000,755 filed Jan. 6, 1987, now abandoned.

This invention is directed to novel amino acid derivatives exhibiting GABA-uptake inhibitory properties and possessing useful pharmacological properties on the central nervous system by selectively enhancing the GABA activity.

SUMMARY OF THE INVENTION

The present invention relates to novel N-(butenyl-substituted)azaheterocyclic carboxylic acids of the general formula I

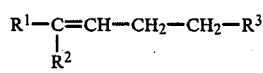 (I)

wherein $R^1$ represents phenyl optionally substituted by one, two or more substituents selected from the group consisting of halogen, lower alkyl, and alkoxy, $R^2$ represents pyrrolyl, furanyl, pyridinyl, pyrazinyl, imidazolyl, pyrazolyl, pyrimidinyl, pyrrolidinyl, tetrahydrofuranyl, piperidinyl, piperazinyl or (lower alkyl)thienyl, each of which may be substituted by one, two or more substituents selected from the group consisting of halogen, lower alkyl, and alkoxy, and $R^3$ represents 3-carboxypiperid-1-yl, 3-carboxy-1,2,5,6-tetrahydropyrid-1-yl or 3-carboxymethylpyrrolidin-1-yl or the corresponding amides or lower alkyl esters, or salts thereof. These compounds have interesting and valuable pharmacological properties.

Preferred compounds are compounds of formula I wherein $R^1$ represents phenyl optionally substituted by one, two or more substituents selected from the group consisting of halogen, $C_{1-6}$-alkyl, and $C_{1-6}$-alkoxy, $R^2$ represents thienyl, pyrrolyl, pyridinyl or furanyl each of which may be substituted with $C_{1-6}$-alkyl or halogen, and wherein $R^3$ represents 3-carboxy-piperidin-1-yl, 3-carboxy-1,2,5,6-tetrahydropyridin-1-yl or 3-carboxymethyl-pyrrolidin-1-yl, or esters, amides, or salts thereof. These compounds have interesting and valuable pharmacological properties.

While all of the components within the above designation exhibit the GABA uptake inhibition, it turns out that tremendous differences exist from compound to compound.

BACKGROUND OF THE INVENTION

In the last decade, intensive pharmacological research concerning γ-aminobutyric acid (hereinafter designated GABA), a neurotransmitter in the central nervous system, has taken place.

Increased GABA'ergic activity is useful in the treatment of anxiety, pain, epilepsy and muscular and movement disorders. Furthermore, these compounds can be used as sedatives.

In U.S. Pat. No. 4,383,999 (Smithkline Beckmann Corporation) some derivatives of N-(4-phenyl-3-butenyl)-azaheterocyclic carboxylic acids which have furthermore, inter alia phenyl, p-fluorophenyl, cyclohexyl or thienyl in the 4-position, are described.

According to J.Pharm.Exp.Therap. 228 (1984), 109 et seq., N(4,4-diphenyl-3-butenyl)nipicotic acid (designated SK&F 89976A), N-(4,4-diphenyl-3-butenyl)guvacine (designated SK&F 100330A), N-(4,4-diphenyl-3-butenyl)-β-homoproline (designated SK&F 10056) and N-(4-sphenyl-4-(2-thienyl)-3-butenyl)nipecotic acid (designated SK&F 100604J) are orally active inhibitors of GABA uptake.

It is further well recognized in the art that β-homoproline, nipecotic acid and guvacine are biological equivalents, at least as far as their GABA-like effects regards. See for example Progress in Medicinal Chemistry 21, 67–120 (1985); ed. Ellis West; Elsevier Science Publishers; Molecular and Cellular Biochemistry 31, 105–121 (1980), and J. Pharm.Exp.Therap., 228 (1984), 109 et seq. In practice of this invention they have been found to be biological equivalents.

DETAILED PRACTICE OF THIS INVENTION

It has now been found that novel compounds of the general formula I exhibit GABA uptake inhibitory properties and possess useful pharmacological properties on the central nervous system, i.e., a selective enhancement of GABA activity. Surprisingly, these effects are superior to those of previously known compounds. Compounds of formula I may be used for treatment of, for example, pain, anxiety, epilepsy, certain muscular and movement disorders, other neurological disorders and as sedatives and hypnotics.

Herein for $R^2$ furanyl is 2-furanyl or 3-furanyl, thienyl is 2-thienyl or 3-thienyl, pyridyl is 2-pyridyl, 3-pyridyl or 4-pyridyl, and pyrrolyl is 2-pyrrolyl or 3-pyrrolyl. Furthermore, halogen is preferably, chloro, bromo and fluoro. The lower alkyl group contains less than 8 carbon atoms, preferably less than 5 carbon atoms, and especially preferred alkyl groups are methyl and ethyl. Examples of preferred substituents are 3-methylthien-2-yl and N-methylpyrrol-2-yl.

$R^1$ is phenyl which may be substituted by one, two or more substituents selected from the group consisting of halogen, lower alkyl, and alkoxy. The lower alkyl group contains less than 8 carbon atoms, preferably less than 5 carbon atoms, and some preferred alkyl groups are methyl and ethyl. The lower alkoxy group contains less than 8 carbon atoms, preferably less than 5 carbon atoms, and some preferred alkoxy groups are methoxy and ethoxy.

Insofar as the inventors hereof are aware, each of the many compounds falling within the generic description will exhibit GABA uptake inhibitory properties, with, however, an extraordinary variation from compound to compound.

A great many of the compounds within the formula I have been prepared, and as has already been indicated a surprisingly large variation in GABA'ergic activity has been found to exist from compound to compound. However, the variations are not generated by differences at $R^3$. To repeat, β-homoproline, nipecotic acid and guvacine are equivalents. It has been found that variations in $R^1$ such as number and locations of substituents on the phenyl ring have a relatively minor effect on the activity.

However, keeping $R^3$ as nipecotic acid relatively small changes in $R^2$ generate substantial variations. Thus, when $R^1$ is phenyl, and when $R^2$ is not substituted, e.g., thien-2-yl an in vitro test value of 470 nM was found. However, when $R^1$ is phenyl and when $R^2$ is changed to the 3-methylthien-2-yl the in vitro test value became 117 nM for the preferred isomer, a much superior result. Moreover, when $R^2$ is 3-methylthien-2-yl and $R^1$ is 2-methylphenyl, an in vitro test value of 74 nM was found. Similar results were obtained when $R^2$ was halogen substituted at the 3-position.

Surprisingly, the superior compounds all turned out to contain an ortho substitution in $R^2$. The same substitution, at the meta position generated an inferior in vitro test value. A sufficient number of compounds according to formula I wherein $R^2$ contained substituents have been synthesized and tested to persuade the inventors hereof that the superior compounds are only ortho substituted in $R^2$, and are single substituted in $R^2$. Such compounds turned out to be better than unsubstituted $R^2$ and far better than di-substituted $R^2$.

Although substituents in $R^1$ have been found to have a relatively minor effect, some preferences exist. Preferred substituents are hydrogen, methyl, ethyl, methoxy, ethoxy and halogen and preferably chloro and bromo. The location on the ring and the substituent as such have been found to have an unpredictable effect, improving or detracting from the desired activity somewhat.

Thus, the preferred compounds of this invention have been found to be compounds of formula I wherein $R^2$ represents furanyl, thienyl, pyridyl, pyrrolyl ortho substituted with $C_{1-7}$-alkyl or halogen, and wherein $R^3$ represents 3-carboxypiperidin-1-yl, 3-carboxy-1,2,5,6-tetrahydropyridin-1-yl or 3-carboxymethyl-pyrrolidin-1-yl, or esters, amides or salts thereof. $R^1$ may vary as above described.

Especially preferred compounds are compounds of formula I wherein $R^2$ represents furanyl, thienyl or pyrrolyl substituted with $C_{1-7}$-alkyl or halogen ortho to the radical position, and wherein $R^3$ represents 3-carboxypiperidin-1-yl, 3-carboxy-1,2,5,6-tetrahydropyridin-1-yl or 3-carboxymethyl-pyrrolidin-1-yl, or esters, amides or salts thereof. $R^1$ may vary as above described.

Some compounds which exhibit superior properties are:

N-(4-(N-Methylpyrrol-2-yl)-4-phenylbut-3-enyl)guvacine,
N-(4-(N-Methylpyrrol-2-yl)-4-phenylbut-3-enyl)nipecotic acid,
N-(4-(N-Methylpyrrol-2-yl)-4-phenylbut-3-enyl)-β-homoproline
N-(4-(2-Methylphenyl)-4-(N-methylpyrrol-2-yl)but-3-enyl)guvacine,
N-(4-(2-Methylphenyl)-4-(N-methylpyrrol-2-yl)but-3-enyl)nipecotic acid,
N-(4-(2-Methylphenyl)-4-(N-methylpyrrol-2-yl)but-3-enyl)-β-homoproline,
N-(4-(3-Methylthien-2-yl)-4-phenylbut-3-enyl)guvacine,
N-(4-(3-Methylthien-2-yl)-4-phenylbut-3-enyl)nipecotic acid,
N-(4-(3-Methylthien-2-yl)-4-phenylbut-3-enyl)-β-homoproline,
N-(4-(2-Methylphenyl)-4-(N-ethylpyrrol-2-yl)but-3-enyl)guvacine,
N-(4-(2-Methylphenyl)-4-(N-ethylpyrrol-2-yl)but-3-enyl)nipecotic acid,
N-(4-(2-Methylphenyl)-4-(N-ethylpyrrol-2-yl)but-3-enyl)-β-homoproline,
N-(4-(2-Methylphenyl)-4-(N-npropylpyrrol-2-yl)but-3-enyl)guvacine,
N-(4-(2-Methylphenyl)-4-(N-npropylpyrrol-2-yl)but-3-enyl)nipecotic acid,
N-(4-(2-Methylphenyl)-4-(N-npropylpyrrol-2-yl)but-3-enyl)-β-homoproline,
N-(4-(2-Ethylphenyl)-4-(N-methylpyrrol-2-yl)but-3-enyl)guvacine,
N-(4-(2-Ethylphenyl)-4-(N-methylpyrrol-2-yl)but-3-enyl)nipecotic acid,
N-(4-(2-Ethylphenyl)-4-(N-methylpyrrol-2-yl)but-3-enyl)-β-homoproline,
N-(4-(2-Methylphenyl)-4-(3-methylthien-2-yl)but-3-enyl)guvacine,
N-(4-(2-Methylphenyl)-4-(3-methylthien-2-yl)but-3-enyl)nipecotic acid,
N-(4-(2-Methylphenyl)-4-(3-methylthien-2-yl)but-3-enyl)-β-homoproline,
N-(4-(2-Ethylphenyl)-4-(3-methylthien-2-yl)but-3-enyl)guvacine,
N-(4-(2-Ethylphenyl)-4-(3-methylthien-2-yl)but-3-enyl)nipecotic acid,
N-(4-(2-Ethylphenyl)-4-(3-methylthien-2-yl)but-3-enyl)-β-homoproline,
N-(4-(2-Ethylphenyl)-4-(3-ethylthien-2-yl)but-3-enyl)-guvacine,
N-(4-(2-Ethylphenyl)-4-(3-ethylthien-2-yl)but-3-enyl)-nipecotic acid,
N-(4-(2-Ethylphenyl)-4-(3-ethylthien-2-yl)but-3-enyl)-β-homoproline,
N-(4-(N-Ethylpyrrol-2-yl)-4-phenylbut-3-enyl)guvacine,
N-(4-(N-Ethylpyrrol-2-yl)-4-phenylbut-3-enyl)nipecotic acid,
N-(4-(N-Ethylpyrrol-2-yl)-4-phenylbut-3-enyl)-β-homoproline,
N-(4-(4-Fluorophenyl)-4-(N-methylpyrrol-2-yl)but-3-enyl)guvacine,
N-(4-(4-Fluorophenyl)-4-(N-methylpyrrol-2-yl)but-3-enyl)nipecotic acid,
N-(4-(4-Fluorophenyl)-4-(N-methylpyrrol-2-yl)but-3-enyl)-β-homoproline,
N-(4-(3-Methylfuran-2-yl)-4-(2-methylphenyl)but-3-enyl)guvacine,
N-(4-(3-Methylfuran-2-yl)-4-(2-methylphenyl)but-3-enyl)nipecotic acid,
N-(4-(3-Methylfuran-2-yl)-4-(2-methylphenyl)but-3-enyl)-β-homoproline,
N-(4-(2,4-Dimethylphenyl)-4-(3-methylthien-2-yl)but-3-enyl)guvacine,
N-(4-(2,4-Dimethylphenyl)-4-(3-methylthien-2-yl)but-3-enyl)nipecotic acid,
N-(4-(2,4-Dimethylphenyl)-4-(3-methylthien-2-yl)but-3-enyl)-β-homoproline,
N-(4-(4-Chloro-2-methylphenyl)-4-(N-methylpyrrol-2-yl)but-3enyl)guvacine,
N-(4-(4-Chloro-2-methylphenyl)-4-(N-methylpyrrol-2-yl)but-3enyl)nipecotic acid,
N-(4-(4-Chloro-2-methylphenyl)-4-(N-methylpyrrol-2-yl)but-3-enyl)-β-homoproline,
N-(4-(4-Chloro-2-methylphenyl)-4-(3-methylthien-2-yl)but-3-enyl)guvacine,
N-(4-(4-Chloro-2-methylphenyl)-4-(3-methylthien-2-yl)but-3-enyl)nipecotic acid,
N-(4-(4-Chloro-2-methylphenyl)-4-(3-methylthien-2-yl)but-3-enyl)-β-homoproline
N-(4-(2-Fluorophenyl)-4-(3-methylthien-2-yl)but-3-enyl)guvacine,
N-(4-(2-Fluorophenyl)-4-(3-methylthien-2-yl)but-3-enyl)nipecotic acid,
N-(4-(2-Fluorophenyl)-4-(3-methylthien-2-yl)but-3-enyl)-β-homoproline,
N-(4-(2,3-Dimethoxyphenyl)-4-(3-methylthien-2-yl)but-3-enyl)guvacine, N-(4-(2,3-Dimethoxyphenyl)-4-(3-methylthien-2-yl)but-3-enyl)nipecotic acid,
N-(4-(2,3-Dimethoxyphenyl)-4-(3-methylthien-2-yl)but-3-enyl)-β-homoproline,
N-(4-(4-Chlorophenyl)-4-(3-methylthien-2-yl)but-3-enyl)guvacine,
N-(4-(4-Chlorophenyl)-4-(3-methylthien-2-yl)but-3-enyl)nipecotic acid,
N-(4-(4-Chlorophenyl)-4-(3-methylthien-2-yl)but-3-enyl)-β-homoproline,
N-(4-(3-Chlorophenyl)-4-(3-methylthien-2-yl)but-3-enyl)guvacine,
N-(4-(3-Chlorophenyl)-4-(3-methylthien-2-yl)but-3-enyl)nipecotic acid,
N-(4-(3-Chlorophenyl)-4-(3-methylthien-2-yl)but-3-enyl)-β-homoproline,
N-(4-(2,5-Dimethoxyphenyl)-4-(3-methylthien-2-yl)but-3-enyl)guvacine,
N-(4-(2,5-Dimethoxyphenyl)-4-(3-methylthien-2-yl)but-3-enyl)nipecotic acid,
N-(4-(2,5-Dimethoxyphenyl)-4-(3-methylthien-2-yl)but-3-enyl)-β-homoproline,
N-(4-(3,5-Dichlorophenyl)-4-(3-methylthien-2-yl)but-3-enyl)guvacine,
N-(4-(3,5-Dichlorophenyl)-4-(3-methylthien-2-yl)but-3-enyl)nipecotic acid,
N-(4-(3,5-Dichlorophenyl)-4-(3-methylthien-2-yl)but-3-enyl)-β-homoproline,
N-(4-(3,4-Dichlorophenyl)-4-(3-methylthien-2-yl)but-3-enyl)guvacine,
N-(4-(3,4-Dichlorophenyl)-4-(3-methylthien-2-yl)but-3-enyl)nipecotic acid,
N-(4-(3,4-Dichlorophenyl)-4-(3-methylthien-2-yl)but-3-enyl)-β-homoproline,
N-(4-(2,4-Dichlorophenyl)-4-(3-methylthien-2-yl)but-3-enyl)guvacine,
N-(4-(2,4-Dichlorophenyl)-4-(3-methylthien-2-yl)but-3-enyl)nipecotic acid,
N-(4-(2,4-Dichlorophenyl)-4-(3-methylthien-2-yl)but-3-enyl)-β-homoproline,
N-(4-(2-Methoxyphenyl)-4-(3-methylthien-2-yl)but-3-enyl)guvacine,
N-(4-(2-Methoxyphenyl)-4-(3-methylthien-2-yl)but-3-enyl)nipecotic acid,
N-(4-(2-Methoxyphenyl)-4-(3-methylthien-2-yl)but-3-enyl)-β-homoproline,
N-(4-(3-Methoxyphenyl)-4-(3-methylthien-2-yl)but-3-enyl)guvacine,
N-(4-(3-Methoxyphenyl)-4-(3-methylthien-2-yl)but-3-enyl)nipecotic acid,
N-(4-(3-Methoxyphenyl)-4-(3-methylthien-2-yl)but-3-enyl)-β-homoproline,
N-(4-(3,5-Dimethoxyphenyl)-4-(3-methylthien-2-yl)but-3-enyl)guvacine,
N-(4-(3,5-Dimethoxyphenyl)-4-(3-methylthien-2-yl)but-3-enyl)nipecotic acid,
N-(4-(3,5-Dimethoxyphenyl)-4-(3-methylthien-2-yl)but-3-enyl)-β-homoproline,
N-(4-(2,6-Dimethylphenyl)-4-(3-methylthien-2-yl)but-3-enyl)guvacine,
N-(4-(2,6-Dimethylphenyl)-4-(3-methylthien-2-yl)but-3-enyl)nipecotic acid,
N-(4-(2,6-Dimethylphenyl)-4-(3-methylthien-2-yl)but-3-enyl)-β-homoproline,
N-(4-(4-Fluoro-2-methylphenyl)-4-(3-methylthien-2-yl)but-3-enyl)-guvacine,
N-(4-(4-Fluoro-2-methylphenyl)-4-(3-methylthien-2-yl)but-3-enyl)nipecotic acid,
N-(4-(4-Fluoro-2-methylphenyl)-4-(3-methylthien-2-yl)but-3-enyl)-β-homoproline,
N-(4-(3-Chloro-2-methylphenyl)-4-(3-methylthien-2-yl)but-3-enyl)-guvacine,
N-(4-(3-Chloro-2-methylphenyl)-4-(3-methylthien-2-yl)but-3-enyl)nipecotic acid,
N-(4-(3-Chloro-2-methylphenyl)-4-(3-methylthien-2-yl)but-3-enyl)-β-homoproline,
N-(4-(3,4-Dimethoxyphenyl)-4-(3-methylthien-2-yl)but-3-enyl)guvacine,
N-(4-(3,4-Dimethoxyphenyl)-4-(3-methylthien-2-yl)but-3-enyl)nipecotic acid,
N-(4-(3,4-Dimethoxyphenyl)-4-(3-methylthien-2-yl)but-3-enyl)-β-homoproline,
N-(4-(3-Chlorothien-2-yl)-4-(2-methylphenyl)but-3-enyl)guvacine,
N-(4-(3-Chlorothien-2-yl)-4-(2-methylphenyl)but-3-enyl)nipecotic acid,
N-(4-(3-Chlorothien-2-yl)-4-(2-methylphenyl)but-3-enyl)-β-homoproline,
N-(4-(3-Bromothien-2-yl)-4-(2-methylphenyl)but-3-enyl)guvacine,
N-(4-(3-Bromothien-2-yl)-4-(2-methylphenyl)but-3-enyl)nipecotic acid,
N-(4-(3-Bromothien-2-yl)-4-(2-methylphenyl)but-3-enyl)-β-homoproline,
N-(4-(3-Chlorothien-2-yl)-4-phenylbut-3-enyl)guvacine,
N-(4-(3-Chlorothien-2-yl)-4-phenylbut-3-enyl)nipecotic acid,
N-(4-(3-Chlorothien-2-yl)-4-phenylbut-3-enyl)-β-homoproline,
N-(4-(3-Bromothien-2-yl)-4-phenylbut-3-enyl)guvacine,
N-(4-(3-Bromothien-2-yl)-4-phenylbut-3-enyl)nipecotic acid,
N-(4-(3-Bromothien-2-yl)-4-phenylbut-3-enyl)-β-homoproline.

Compounds of formula I may exist as geometric optical isomers and all isomers and mixtures thereof are included herein. Isomers may be separated by means of standard methods such as chromatographic techniques or fractional crystallisation.

One embodiment of this invention is non-toxic pharmaceutically acceptable salts of compounds of formula I. Salts include those derived from inorganic or organic acids such as hydrochloric, hydrobromic, sulfuric, phosphoric, acetic, lactic, maleic and phthalic acid.

Compounds of formula I may be prepared by N-alkylation of a compound of the general formula II

$$H-R'^3 \qquad (II)$$

wherein $R'^3$ has the same meaning as $R^3$ with the proviso that the carboxy group is protected, for example, by an ester group, with a compound of the general formula III

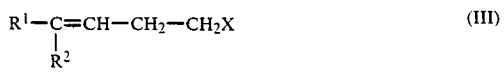

$$R^1-C=CH-CH_2-CH_2X \qquad (III)$$
$$\quad\;\; |$$
$$\quad\;\; R^2$$

wherein $R^1$ and $R^2$ are as defined in claim 1, and X represents halogen. This reaction may be carried out in an inert solvent in the presence of an alkali metal carbonate, for example, potassium carbonate at, for example, room temperature, for from about 1 to 12 days. The solvent may conveniently be acetone or N,N-dimethylformamide. Compounds of formula I may be prepared by hydrolysis of the resulting ester, preferably at room temperature in a mixture of an aqueous sodium hydroxide solution and an alcohol such as methanol or ethanol for from about 0.5 to 4 h.

Compounds of formula III may be prepared by reacting the appropriate disubstituted ketones with a Grignard reagent, i.e., cyclopropyl magnesium bromide, followed by ring opening of the intermediate cyclopropyl carbinol derivative by treatment with hydrogen bromide in acetic acid. Alternative conditions involve the use of trimethylsilyl chloride and lithium iodide or trimethylsilyl bromide in, for example, dichloromethane, at f.ex. −70° to 20° C.; or compounds of formula III may be prepared by reacting a ketone of the general formula IV

$$R^4-C(O)-CH(CH_2)_2 \qquad (IV)$$

wherein $R^4$ is $R^1$ or $R^2$ and $R^1$ and $R^2$ are as defined above, with an aryl Grignard reagent ($R^4$-MgBr for example, wherein $R^4$ is as defined above) in f.ex. tetrahydrofuran, at f.ex. −70° to 40° C., followed by ring opening and halogenation of the intermediate carbinol with a trialkylsilylhalogenide in f.ex. dichloromethane at f.ex. −70° to 20° C.; or compounds of formula III may be prepared by reacting alcohols of the general formula V

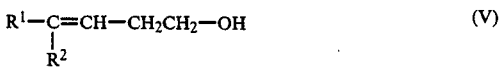
$$R^1-C=CH-CH_2CH_2-OH \qquad (V)$$
$$\phantom{R^1-C=}|\phantom{CH-CH_2CH_2-OH}$$
$$\phantom{R^1-C=}R^2$$

wherein $R^1$ and $R^2$ each are as defined above with a tosylchloride in f.ex. pyridine at f.ex. −20° to 20° C.

Compounds of formula V may be prepared by reacting a compound of formula VI

$$R^1R^2COCH_2CH_2CH_2 \qquad (VI)$$

wherein $R^1$ and $R^2$ each are as defined above with dilute acid, f.ex. ethanolic aqueous hydrochloric acid at f.ex. 40° to 80° C. for 1 to 10 h.

Compounds of formula VI may be prepared by reacting a compound of formula VII

$$R^1-CO-CH_2CH_2CH_2X \qquad (VII)$$

wherein $R^1$ is as defined above and X is halogen, with an aryl Grignard reagent e.g. $R^2$MgBr in f.ex. tetrahydrofuran at reflux temperature for 1 to 10 h.

Compounds of formula I are useful because they possess pharmacological activity in man. In particular, the compounds of formula I are useful as inhibitors of GABA uptake.

For the above indications, the dosage will vary depending on the compound of formula I employed, on the mode of administration and on the therapy desired. However, in general, satisfactory results are obtained with a dosage of from about 15 mg to about 2 g of compounds of formula I, conveniently given from 1 to 5 times daily, optionally in sustained release form. Usually, dosage forms suitable for oral administration comprise from about 25 mg to about 1 g of the compounds of formula I admixed with a pharmaceutical carrier or diluent. No toxic effects have been observed at these levels.

The compounds of formula I may be administered in pharmaceutically acceptable acid addition salt form.

Such acid addition salt forms exhibit approximately the same order of activity as the free base forms.

This invention also relates to pharmaceutical compositions comprising a compound of formula I or a pharmaceutically acceptable salt thereof and, usually, such compositions also contain a pharmaceutical carrier or diluent. The compositions of this invention may be prepared by conventional techniques to appear in conventional forms, for example, capsules or tablets.

The pharmaceutical carrier employed may be conventional solid or liquid carriers. Examples of solid carriers are lactose, terra alba, sucrose, talc, gelatin, agar, pectin, acacia, magnesium stearate and stearic acid. Examples of liquid carriers are syrup, peanut oil olive oil and water. Similarly, the carrier or diluent may include any time delay material well known to the art such as glyceryl monostearate or glyceryl distearate, alone or mixed with a wax.

If a solid carrier for oral administration is used, the preparation can be tabletted, placed in a hard gelatin capsule in powder or pellet form or in the form of a troche or lozenge. The amount of solid carrier will vary widely but, usually, will be from about 25 mg to about 1 g. If a liquid carrier is used, the preparation may appear in the form of a syrup, emulsion, soft gelatin capsule or sterile injectable liquid such as an aqueous or non-aqueous liquid suspension.

The pharmaceutical compositions of this invention can be made following the conventional techniques of the pharmaceutical industry involving mixing, granulating and compressing or variously mixing and dissolving the ingredients as appropriate to give the desired end product.

The route of administration may be any route which effectively transports the active compound to the appropriate or desired place, such as orally or parenterally, the oral route being preferred.

The features disclosed in the foregoing description and in the following examples and claims may, both separately and in any combination thereof, be material for realising the invention in diverse forms thereof.

The process for preparing compounds of formula I and preparations containing them is further illustrated in the following examples, which, however, are not to be construed as limiting. The examples illustrate some preferred embodiments.

Hereinafter T.l.c. is thin layer chromatography, THF is tetrahydrofuran and EtOH is ethanol.

EXAMPLE 1

Cyclopropyl-(N-methylpyrrol-2-yl)phenylmethanol

To a suspension of magnesium turnings (5.29 g, 0.22 mole) in anhydrous tetrahydrofuran (70 ml), cyclopropyl bromide (26.35 g, 0.22 mole) in tetrahydrofuran (50 ml) was added dropwise under nitrogen. The reaction mixture was heated at reflux for one h after the initial exotherm had subsided before (N-methylpyrrol-2-yl)phenylketone (13.3 g, 0.072 mole) (J. White and G. McGillivray, J. Org. Chem., (1977), 42, 4248, R. Greenhouse and C. Ramirez, J. Org. Chem., (1985), 50, 2961) in anhydrous tetrahydrofuran (50 ml ) was introduced dropwise. After heating the reaction mixture at reflux for 3 h it was cooled and saturated, aqueous ammonium chloride solution (95 ml) and water (150 ml) were added. The mixture was extracted with ethyl acetate (3×200 ml) and the combined extracts were dried (MgSO₄). Flash chromatography of the residue on evaporation on silica gel eluting with heptane/tetrahydrofuran (9:1) provided the title compound as an oil (9.9 g, 46%) which solidified on standing. T.l.c. rf=0.35 (SiO₂, heptane/THF (7:3)).

Ring opening of cyclopropylcarbinol: Method A

1-Bromo-4-(N-methylpyrrol-2-yl)-4-phenylbut-3-ene

Cyclopropyl-(N-methylpyrrol-2-yl)phenylmethanol was dissolved in acetic acid (60 ml) and a mixture of acetic acid (30 ml) and 48% hydrobromic acid (15 ml) was added at 5° C. The mixture was stirred for 30 min. and poured into water (300 ml). The resultant emulsion was extracted with ethyl acetate (2×100 ml). The combined organic layers were washed with saturated sodium bicarbonate solution and brine and dried (Na₂SO₄). The concentrate, containing some acetic acid, was passed through a silica column (Merck Art 9385) with heptane/tetrahydrofuran (19:1) as eluent. After further flash chromatography in the same solvent system, the pure bromide (Z isomer) was obtained. T.l.c. rf=0.35 (SiO₂, heptane/THF (9;1)).

Method B (G. Balme, G. Fournet and J. Gore, Tetrahedron. Lett., (1905), 1907)

4-(N-Methylpyrrol-2-yl)-4-phenylbut-3-en-1-yl chloride and iodide

Cyclopropyl-(N-methylpyrrol-2-yl)phenylmethanol (6.46 g, 28.4 mmol) was dissolved in dichloromethane (200 ml) and lithium iodide (4.56 g. 31.4 mmol) was introduced. The mixture was cooled to 0° C., and chlorotrimethylsilane (3.6 ml, 28.4 mmol) was added dropwise. After 2 h at 0° C., the reaction mixture was filtered and evaporated to a dark green oil (7.28 g). Flash chromatography on silica gel (Merck Art 9385) eluting with heptane/tetrahydrofuran (19:1) provided the title compounds as an oil (6.3 g, 64%) (a mixture of E and Z isomers). T.l.c. rf=0.29 (SiO₂, heptane/THF (9:1)).

R-N-(4-(N-Methylpyrrol-2-yl)-4-phenylbut-3-en-1-yl)nipecotic acid ethyl ester 4-(N-Methylpyrrol-2-yl)-4-phenylbut-3-en-1-yl chloride and iodide (3.0 g, 8.7 mmol) were dissolved in anhydrous acetone (50 ml) and dried potassium carbonate (4.8 g, 34.8 mmol), sodium iodide (1.4 g, 8.7 mmol) and the R-enantiomer of ethyl nipecotate (1.462 g, 9.3 mmol) (A. M. Akkerman et al., Rec.Trav.Chem., 1951, 70, 899; G. Bettoni et al. Gazz.Chem.Ital., 1972, 102, 189) was added. The suspension was stirred at room temperature for 10 days, filtered and evaporated to a gummy residue which was purified by flash chromatography on silica gel (Merck Art 9385). Elution with heptane/tetrahydrofuran (19:1) provided the title ester (1.74 g, 54%) as an oil T.l.c. rf=0.06 (SiO₂), heptane/THF (9:1)).

R-N-(4-(N-Methylpyrrol-2-yl)-4-phenylbut-3-en-1-yl)nipecotic acid hydrochloride (NO-05-0356)

R-N-(4-(N-Methylpyrrol-2-yl)-4-phenylbut-3-en-1-yl)nipecotic acid ethyl ester (1.74 g, 4.7 mmol) was dissolved in ethanol (50 ml) and 10N sodium hydroxide solution (8.9 ml) was added. The solution was stirred at room temperature for 30 min. and cooled to 0° C. The pH was adjusted to 5 with 4N hydrochloric acid solution, and the solution was extracted with dichloromethane (4×25 ml). The combined extracts were washed with water (10 ml) and dried (MgSO₄). The residue on evaporation was treated with water (100 ml) and activated charcoal. Filtration through a millipore filter gave a solution which was freeze-dried to give the product as a cream solid (1.53 g, 82%). Melting point: 67° C. dec. It was found that the E and Z isomers could be separated by HPLC.

EXAMPLE 2

N-(4-(N-Methylpyrrol-2-yl)-4-phenylbut-3-en-1-yl)nipecotic acid ethyl ester

1-Bromo-4-(N-methylpyrrol-2-yl)-4-phenylbut-3-ene (4.58 g, 15.9 mmol) was dissolved in anhydrous acetone (115 ml) and dried potassium carbonate (8.78 g, 63.6 mmol) was introduced, followed by ethyl nipecotate (3.25 g, 20.7 mmol). The reaction mixture was stirred at room temperature for 12 days, filtered and evaporated to give a brown oil (6.4 g). Column chromatography on silica gel (Merck Art 15111) eluting with heptane/tetrahydrofuran (19:1) provided the title compound as an oil (3.68 g, 63%). T.l.c. rf=0.31 (SiO₂, THF/heptane (3:7)).

N-(4-N-Methylpyrrol-2-yl)-4-phenylbut-3-en-1-yl)nipecotic acid hydrochloride (NO-05-0165)

N-(4-(N-Methylpyrrol-2-yl)-4-phenylbut-3-en-1-yl)nipecotic acid ethyl ester (2.75 g, 7.5 mmol) was dissolved in ethanol (70 ml). 10N sodium hydroxide solution (14 ml) was introduced, and the solution was stirred for 30 min. at room temperature before being cooled to 0° C. The pH was adjusted to 7 with 4N hydrochloric acid solution, and the reaction mixture was extracted with dichloromethane (4×100 ml) (emulsion). The combined organic extracts were washed with a mixture of saturated brine (20 ml) and water (20 ml). The layers were separated, and the aqueous phase was washed with dichloromethane (100 ml). The combined extracts were dried (Na₂SO₄) and filtered through "hyflo". The filtrate was evaporated and the residue dissolved in 150 ml water, decolourised (charcoal) and freeze-dried. The title amino acid was obtained as a dense white powder (Z isomer) (1.83 g, 72%). T.l.c. rf=0.33 (SiO₂, dichloromethane/methanol (4:1)).

EXAMPLE 3

2-Benzoyl-N-ethylpyrrole

2-Benzoylpyrrole (ref. as in Example 1) (10.27 g, 0.06 mole) was dissolved in dry N,N-dimethylformamide (120 ml) and combined with sodium hydride (2.016 g, 0.084 mole) (60% oil dispersion) in dry N,N-dimethylformamide (120 ml). The reaction mixture was stirred at room temperature for 18 h and water (100 ml) was added. The reaction mixture was extracted with diethyl ether (3×100 ml) and the combined extracts were washed with water (200 ml). The organic layer was dried (MgSO₄) and evaporated to give the title compound as an oil (11.74 g, 98%). T.l.c. rf=0.53 (SiO₂, dichloromethane/methanol (98:2)).

This ketone was converted into a mixture of 4-(N-ethylpyrrol-2-yl)-4-phenylbut-3-en-1-yl chloride and iodide by the method described in Example 1 (using Method B).

R-N-(4-(N-Ethylpyrrol-2-yl)-4-phenylbut-3-en-1-yl)nipecotic acid ethyl ester 4-(N-Ethylpyrrol-2-yl)-4-phenylbut-3-en-1-yl chloride and iodide (3.16 g, 9 mmol) were dissolved in anhydrous acetone (50 ml) and dried potassium carbonate (4.97 g, 36 mmol), sodium iodide (2.7 g, 18 mmol) and the R-enantiomer of ethyl nipecotate (1.93 g, 13.7 mmol) were introduced. The suspension was stirred at room temperature for 10 days, filtered and evaporated to a residue. The residue was purified by column chromatography on silica gel (Merck Art 9385) eluting with heptane/tetrahydrofuran (19:1), providing the title ester (1.50 g, 43%) as a gum. T.l.c. rf=0.21 (SiO$_2$, heptane/THF (4:1)).

R-N-(4-(N-Ethylpyrrol-2-yl)-4-phenylbut-3-en-1-yl)nipecotic acid

R-N-(4-(N-Ethylpyrrol-2-yl)-4-phenylbut-3-en-1-yl)nipecotic acid ethyl ester (0.14 g, 0.4 mmol) was hydrolysed by the method outlined in Example 1. The title acid was obtained as a freeze-dried solid (Z isomer) (54 mg, 33%); m.p. 56.5°–60° C. (decomposition).

EXAMPLE 4

N-(4-(N-Methylpyrrol-2-yl)-4-phenylbut-3-en-1-yl)guvacine methyl ester 4-(N-Methylpyrrol-2-yl)-4-phenylut-3-en-1-yl chloride and iodide (1.46 g, 4.3 mmol) (Example 1) were dissolved in anhydrous acetone (30 ml) and dried potassium carbonate (2.37 g, 17.2 mmol), sodium iodide (0.645 g, 4.3 mmol) and guvacine methyl ester hydrochloride (0.995 g, 5.6 mmol) were added. The suspension was stirred at room temperature for 5 days, and worked up as described in Example 1 to give the title ester (1.1 g, 72%) as a fawn oil (mixture of E and Z isomers). T.l.c. rf=0.05 (SiO$_2$, heptane/THF (9:1)).

N-(4-(N-Methylpyrrol-2-yl)-4-phenylbut-3-en-1-yl)guvacine hydrochloride (mixture of E and Z isomers) (NO-05-0387)

N-(4-(N-Methylpyrrol-2-yl)-4-phenylbut-3-en-1-yl)guvacine methyl ester (1.02 g, 2.9 mmol) was hydrolysed by the method outlined in Example 1. The title acid was obtained as a freeze dried solid (0.64 g, 52%); melting point: 81.5°–84° C. (E and Z isomers).

N-(4-(N-Methylpyrrol-2-yl)-4-phenylbut-3-en-1-yl)guvacine methyl ester

1-Bromo-4-(N-methylpyrrol-2-yl)-4-phenylbut-3-ene (0.60 g, 2.08 mmol) was dissolved in anhydrous acetone (20 ml) and dried potassium carbonate (1.10 g, 8 mmol) was introduced, followed by guvacine methyl ester hydrochloride (0.37 g, 2.08 mmol). The reaction mixture was stirred at room temperature for 10 days and worked up as described in Example 1 to give the title ester (Z isomer) (380 mg, 52%) as an oil. T.l.c. rf=0.03 (SiO$_2$, heptane/THF (9:1)).

N-(4-(N-Methylpyrrol-2-yl)-4-phenylbut-3-en-1-yl)guvacine hydrochloride (Z-isomer) NO-05-0227

N-(4-(N-Methylpyrrol-2-yl)-4-phenylbut-3-en-1-yl)guvacine methyl ester was hydrolysed by the method outlined in Example 1. The title acid was obtained as a freeze-dried white powder (60 mg, 38%); melting point: 70° C.

EXAMPLE 5

Cyclopropylphenyl (4-pyridyl)methanol

Magnesium turnings (2.65 g, 0.109 mole) in dry tetrahydrofuran (50 ml) was treated dropwise with cyclopropyl bromide (13.2 ml, 0.109 mole). The reaction mixture was heated at reflux for 1 h after the initial exotherm had subsided and then 4-benzoylpyridine (10 g, 0.0545 mole) was introduced. Heating at reflux was continued for 2 h, the reaction mixture was cooled and saturated ammonium chloride solution (80 ml) was added. This aqueous phase was extracted with ethyl acetate (3×200 ml) and the combined extracts were dried (MgSO$_4$). Evaporation gave a crude solid residue (6.23 g) which was recrystallised from toluene to give the title alcohol (2.57 g, 21%), m.p. 171°–172° C. T.l.c. rf=0.065 (SiO$_2$, THF/heptane (3:7)).

1-Bromo-4-phenyl-4-(4-pyridyl)but-3-ene

Cyclopropylphenyl (4-pyridyl)methanol (2.4 g, 10.6 mmol) was dissolved in acetic acid (25 ml). The solution was cooled to 0° C. A 47% solution of hydrogen bromide (5 ml) was added and the reaction mixture was stirred at room temperature for 3.5 h, and at 40° C. for 1 h. The reaction mixture was poured into water (100 ml) and this aqueous phase was extracted with ethyl acetate (3×50 ml). The combined organic extracts were washed with saturated sodium bicarbonate solution (40 ml) and saturated brine (40 ml) and dried (MgSO$_4$). Evaporation gave a crude product (3.26 g) which was purified by flash chromatography on silica gel (Merck Art 9385). Elution with heptane/ethyl acetate (7:3) provided an oil (1.38 g, 45%) which solidified on standing. T.l.c. rf=0.13 (SiO$_2$, heptane/ethyl acetate (7:3)).

N-(4-Phenyl-4-(4-pyridyl)but-3-en-1-yl)nipecotic acid, ethyl ester

1-Bromo-4-phenyl-4-(4-pyridyl)but-3-ene (1.0 g, 3.5 mmol), ethyl nipecotate (0.72 g, 4.6 mmol) and potassium carbonate (1.93 g, 14.0 mmol) in acetone (30 ml) were stirred at room temperature for 5 days. The reaction mixture was filtered, and evaporated to a residue which was purified by flash chromatography on silica gel (Merck Art 9385). Elution with dichloromethane/ethanol/25% ammonium solution (190:9:1) provided the title compound as an oil. T.l.c. rf=0.23 (SiO$_2$, CH$_2$Cl$_2$/EtOH/NH$_3$ (190:9:1)).

N-(4-Phenyl-4-(4-pyridyl)but-3-en-1-yl)nipecotic acid hydrochloride (NO-05-0358)

N-(4-Phenyl-4-(4-pyridyl)but-3-en-1-yl)nipecotic acid ethyl ester was hydrolysed by the method outlined in Example 1. The title acid was obtained as a freeze dried solid.

EXAMPLE 6

2-Methylphenyl-(4-pyridyl)methanol

Magnesium turnings (3.2 g, 0.131 mole) in dry tetrahydrofuran (50 ml) were treated dropwise with 2-bromotoluene (15 g, 0.087 mole). The reaction mixture was heated at reflux for 1 h after the initial reflux had subsided. After cooling, 4-pyridylcarboxaldehyde (14.38 g, 0.131 mole) in dry tetrahydrofuran (30 ml) was introduced slowly, and subsequently the reaction mixture was heated at reflux for 2 h. The reaction was worked up as in Example 5 (Grignard reaction) to give the title alcohol (5.92 g, 34%). T.l.c. rf=0.24 (SiO$_2$, ethyl acetate).

4-(2-Methylbenzoyl)pyridine

Pyridinium chlorochromate (9.29 g, 43.1 mmol) was dissolved in dichloromethane (50 ml) and a solution of 2-methylphenyl-(4-pyridyl)methanol (5.72 g, 28.7 mmol) in dichloromethane (30 ml) was added. The reaction mixture became dark immediately, and was stirred for 2 h at room temperature. Diethyl ether (350 ml) was added, and the reaction mixture was filtered through "hyflo" and evaporated to a dark oil (11.26 g). Flash chromatography on silica gel (Merck Art 9385) eluting with heptane/tetrahydrofuran (4:1) provided the title compound (2.74 g, 48%) as an oil. T.l.c. rf=0.45 (SiO$_2$, ethyl acetate).

This ketone was converted into 1-bromo-4-(2-methylphenyl)-4-(4-pyridyl)but-3-ene by the method described in Example 1 (Method A).

N-(4-(2-Methylphenyl)-4-(4-pyridyl)but-3-en-1-yl)nipectic acid ether ester

1-Bromo-4-(2-methylphenyl)-4-(4-pyridyl)but-3-ene (1.9 g, 7.6 mmol) was dissolved in anhydrous acetone (30 ml) and dried potassium carbonate (4.2 g, 30.4 mmol) and ethyl nipecotate (2.39 g, 15.2 mmol) were introduced. The suspension was stirred at room temperature for 18 h, filtered and evaporated to a residue. The residue was purified by "flash" chromatography on silica gel (Merck Art 9385) eluting with heptane/tetrahydrofuran (7:3) to provide the title ester (0.67 g, 41%) as a reddish oil (a mixture of E and Z isomers). T.l.c. rf=0.08 (SiO$_2$; heptane/THF (7:3)).

N-(4-(2-Methylphenyl)-4-(4-pyridyl)but-3-en-1-yl)nipecotic acid

N-(4-(2-Methylphenyl)-4-(4-pyridyl)but-3-en-1-yl)nipecotic acid ethyl ester (0.67 g, 1.8 mmol) was dissolved in ethanol (20 ml) and 10N sodium hydroxide solution (3.42 ml) was added. The solution was stirred at room temperature for 0.5 h, and the pH was adjusted to 5 with 4N hydrochloric acid. The solution was applied to a column of Dowex 50WX8 ion exchange resin (H$^+$ form). Elution with water followed by dilute ammonia solution provided the title acid (180 mg, 30%).

EXAMPLE 7

2-Methylphenyl-(3-methyl-2-thienyl)methanol

The title compound was prepared from 2-bromotoluene (35.55 g, 0.208 mole), magnesium turnings (5.1 g, 0.208 mole) and 3-methylthiophene-2-aldehyde (23.6 g, 0.187 mole) by the method described in Example 6, using diethyl ether (150 ml) as solvent. The yield was 36.0 g (88%). T.l.c. rf=0.39 (SiO$_2$, heptane/THF (7:3)).

3-Methyl-2-(2-methylbenzoyl)thiophene

2-Methylphenyl-(3-methyl-2-thienyl)methanol (36.0 g, 0.165 mole) was dissolved in dichloromethane (400 ml) and manganese dioxide (58 g, 0.667 mole) was added. The reaction mixture was heated at reflux for 18 h, cooled and further manganese dioxide (30 g, 0.34 mole) was introduced; reflux was continued for a further 18 h. The mixture was filtered and evaporated to a residue (32 g) which was distilled in vacuo (0.2 mm Hg). Fractions boiling at 100°–120° C. (4.8 g) and 120°–132° C. (21.0 g) were collected, giving the title compound as an oil (25.8 g, 72%).

The ketone was converted into 1-bromo-4-(2-methylphenyl)-4-(3-methyl-2-thienyl)but-3-ene by the method described in Example 1 (Method A).

R-N-(4-(2-Methylphenyl)-4-(3-methyl-2-thienyl)but-3-en-1-yl)nipecotic acid ethyl ester 1-Bromo-4-(2-methylphenyl)-4-(3-methyl-2-thienyl)-but-3-ene (3.0 g, 9.34 mmol) was dissolved in anhydrous acetone (40 ml) and dried potassium carbonate (1.38 g, 10 mmol), potassium iodide (0.2 g, 1 mmol) and the R-enantiomer of ethyl nipecotate (1.57 g, 10 mmol) were introduced. The suspension was stirred at room temperature for 18 h, filtered and evaporated to a residue. The residue was purified by "flash" chromatography on silica gel (Merck Art 9385) eluting with heptane/tetrahydrofuran (4:1), to provide the title ester (2.4 g, 65%) as an oil T.l.c. rf=0.40 (SiO$_2$, heptane/THF (7:3)).

R-N-(4-(2-Methylphenyl)-4-(3-methyl-2-thienyl)but-3-en-1-yl)nipecotic acid (NO-05-0340)

R-N-(4-(2-Methylphenyl)-4-(3-methyl-2-thienyl)but-3-en-1-yl)nipecotic acid ethyl ester (1.4 g, 3.52 mmol) was hydrolysed by the method outlined in Example 1. The title acid was obtained as a solid (1.1 g, 85%); melting point: 65°–57° C. The hydrochloride salt was obtained when adjusting pH to 1 before work-up. Melting point of hydrochloride: 192°–5° C. (Acetone).

EXAMPLE 8

Cyclopropyl-2-furylphenylmethanol

To a suspension of magnesium turnings (0.26 g, 10.5 mmol) in anhydrous tetrahydrofuran (6 ml) cyclopropyl bromide (1.28 g, 10.5 mmol) in tetrahydrofuran (5 ml) was added dropwise under nitrogen. The reaction mixture was heated at reflux for 1 h after the initial exotherm had subsided before 2-benzoylfuran (12 g, 7.0 mmol) was added as a solution in tetrahydrofuran (10 ml). The reaction mixture was worked up as described in Example 1 to give the title alcohol as an oil. T.l.c. rf=0.23 (SiO$_2$, heptane/THF (7:3)).

This compound was converted directly into 1-bromo-4-(2-furanyl)-4-phenylbut-3-ene by the method described in Example 1 (Method A).

N-(4-(2-Furanyl)-4-phenylbut-3-en-1-yl)nipecotic acid ethyl ester

1-Bromo-4-(2-furanyl)-4-phenylbut-3-ene (0.23 g, 0.83 mmol) was dissolved in anhydrous acetone (10 ml) and dried potassium carbonate (0.46 g, 3.32 mmol) was added, followed by ethyl nipecotate (0.16 g, 1 mmol). The suspension was stirred at room temperature for 9 days, filtered and evaporated to a residue. The residue was purified by column chromatography on silica gel (Merck Art 9385), eluting with heptane/tetrahydrofuran (7:3), to provide the title ester (140 mg, 47%) as an oil. T.l.c. rf=0.36 (SiO$_2$, heptane/THF (7:3)).

N-(4-(2-Furanyl)-4-phenylbut-3-ene-1-yl)nipecotic acid

N-(4-(2-Furanyl)-4-phenylbut-3-en-1-yl)nipecotic acid ethyl ester (130 mg, 0.36 mmol) was hydrolysed by the method described in Example 1. The title acid was obtained as a freeze dried solid. T.l.c. rf=0.43 (SiO$_2$, methanol).

EXAMPLE 9

Cyclopropyl-(2-methylphenyl)-(N-methylpyrrol-2-yl)methanol

To a suspension of magnesium turnings (1.72 g, 0.071 mole) in anhydrous tetrahydrofuran (20 ml), 2-bromotoluene (12.1 g, 0.071 mole) in tetrahydrofuran (100 ml) was added dropwise under nitrogen. The reaction mixture was heated at reflux for 1 h after the initial exotherm had subsided before cyclopropyl-(N-methylpyrrol-2-yl)ketone (7.1 g, 0.047 mole) (*J. Org. Chem.*, (1971), 36, 2897; *J.Org.Chem.* (1980), 45, 3172) in anhydrous tetrahydrofuran (100 ml) was introduced. After heating the reaction mixture at reflux for 2 h it was left overnight at room temperature. Saturated, aqueous ammonium chloride solution (100 ml) was added, and the mixture was extracted with diethyl ether (3×200 ml). The combined extracts were dried (MgSO$_4$) and the solvents evaporated. The residue was flash chromatografied on silica gel eluting with n-heptane/tetrahydrofuran (19:1) providing the title compound as a solid (10.9 g).

1-Bromo-4-(2-methylphenyl)-4-(N-methylpyrrol-2-yl)but-3-ene

Cyclopropyl-(2-methylphenyl)-(N-methylpyrrol-2-yl)methanol (9.9 g, 0.041 mole) was dissolved in dichloromethane (250 ml) and cooled to −70° C. under nitrogen. Bromotrimethylsilane (6.4 g, 0.042 mole) in dichloromethane (250 ml) was added within 30 min. The reaction mixture was stirred at −70° C. for another 90 min. Pyridine (3.5 ml) was added and when the mixture had reached room temperature, saturated sodium bicarbonate solution (100 ml) was added. The phases were separated and the organic phase was dried (MgSO$_4$) and evaporated leaving the title compound as an oil (10.9 g).

R-N-(4-(2-methylphenyl)-4-(N-methylpyrrol-2-yl)but-3-en-1-yl)nipecotic acid ethyl ester 1-bromo-4-(2-methylphenyl)-4-(N-methylpyrrol-2-yl)but-3-ene 11.9 g, 0.039 mole) was dissolved in acetone (100 ml) and potassium carbonate (21.5 g, 0.16 mole) and the R-enantiomer of ethyl nipecotate (9.2 g, 0.058 mole) was added. The suspension was stirred at room temperature for 72 h, filtered and evaporated to an oily residue, which was purified by flash chromatography on silica gel. Elution with n-heptane/tetrahydrofuran (9:1) provided the title ester as an oil (11.2 g). A sample of this ester (8.2 g, 0.022 mole) was dissolved in degassed dry toluene (30 ml) and methanol (0.87 ml) was added. A solution of chlorotrimethylsilane (2.26 g, 0.020 mole) in dry toluene (10 ml) was added and the mixture was left at 4° C. for crystallization. The precipitate was isolated and washed with cold toluene leaving the title ester hydrochloride as a white solid (7.2 g), M.p.=133°-6° C.

R-N-(4-(2-methylphenyl)-4-(N-Methylpyrrol-2-yl)but-3-en-1-yl) nipecotic acid hydrochloride (NO-05-0713)

R-N-(4-(2-methylphenyl)-4-(N-methylpyrrol-2-yl)but-3-en-1-yl) nipecotic acid ethyl ester (0.84 g, 0.0022 mole) was hydrolysed to the title compound (0.7 g) by a similar method as described in Example 2. HPLC rf=15.9 minutes (5 μm C-18 (4.6 mm×250 mm) nucleosil column, 20-70% gradient of acetonitrile/0.045M ammonium acetate pH 4.5 within 30 min.).

EXAMPLE 10

R-N-(4-(2,4-dimethylphenyl)-4-(3-methyl-2-thienyl)but-3-en-1-yl)nipecotic acid hydrochloride (NO-05-0963)

A solution of cyclopropyl(2,4-dimethylphenyl)(3-methyl-2-thienyl)methanol (7.0 g, 0.026 mole; obtained by the method described in Example 7) in dichloromethane (125 ml) was cooled to 10° C. and bromotrimethylsilane (4.0 g, 0.026 mole) in dichloromethane (50 ml) was added dropwise keeping the temperature at about 10° C. When addition was complete, water was added (250 ml) and the phases were separated. The aqueous phase was extracted with dichloromethane (25 ml). The combined organic phases was washed with a saturated sodium bicarbonate solution, brine and dried over sodium sulphate. The solvent was removed in vacuo leaving 1-bromo-4-(2,4-dimethylphenyl)-4-(3-methyl-2-thienyl)but-3-ene (8.7 g) as an oil. This bromide was converted by the method described in Example 7 into the title acid hydrochloride, M.p.=200°-201° C. (i-Propanol).

EXAMPLE 11

2-(3-methyl-2-thienyl)-2-phenyltetrahydrofuran and 4-(3-methyl-2-thienyl)-4-phenylbut-3-en-1-ol 2-bromo-3-methylthiophene (12.0 g, 0.067 mole) and magnesium turnings (1.83 g, 0.075 mole) were mixed in dry tetrahydrofuran (100 ml). After the initial violent exotherm had died down, the reaction mixture was heated for 2 h at reflux and cooled. A solution of γ-chlorobutyrophenone (13.7 g, 0.072 mole) in dry tetrahydrofuran (100 ml) was added dropwise and the mixture was heated at reflux for 2 h after the exotherm had died down. The cooled mixture was treated with saturated ammonium chloride solution (50 ml) and water (200 ml) and extracted with ethyl acetate (3×200 ml). The combined extracts were dried (Na$_2$SO$_4$) and evaporated. NMR indicated that the residue contained 2-(3-methyl-2-thienyl)-2-phenyltetrahydrofuran. To this product was added 2N hydrochloric acid solution (20 ml) and ethanol (150 ml) and the solution was heated at 80° C. for 2 h. Tetrahydrofuran (50 ml) and further 2M hydrochloric acid solution (10 ml) were added and heating was continued for 4 h. The solution was cooled and evaporated to a residue. Saturated sodium bicarbonate solution (200 ml) was introduced and the mixture was extracted with ethyl acetate (3×200 ml). The combined extracts were dried (MgSO$_4$) and evaporated to a gum, which was purified by flash chromatography on silica gel (Art 9385).

Elution with heptane/ethyl acetate (6:1→3:1) provided first a fraction containing 2-(3-methyl-2-thienyl)-2-phenyltetrahydrofuran (7.6 g, 46%) and second a fraction containing 4-(3-methyl-2-thienyl)-4-phenylbut-3-en-1-ol (6.0 g, 34%).

1-chloro-4-(3-methyl-2-thienyl)-4-phenylbut-3-ene and (4-(3-methyl-2-thienyl)-4-phenylbut-3-en-1-yl)p-toluenesulphonate 4-(3-methyl-2-thienyl)-4-phenylbut-3-en-1-ol obtained above (1.47 g, 0.006 mole) and p-toluenesulphonyl chloride (1.71 g, 0.009 mole) were dissolved in ethanol-free chloroform (30 ml) and pyridine (0.972 ml, 0.012 mole). This solution was stirred at room temperature for 4 days, and at reflux for 2.5 days. The reaction mixture was poured into a mixture of water (30 ml) and saturated sodium bicarbonate solution (30 ml). The chloroform layer was separated and the aqueous layer was extracted further with dichloromethane (25 ml) and ethyl acetate (30 ml). The combined organic extracts were dried (MgSO$_4$) evaporated and purified by flash chromatography on silica gel (Art 9385). Elution with heptane/tetrahydrofuran (30:1) provided 1-chloro-4-(3-methyl-2-thienyl)-4-phenylbut-3-ene as an oil (1.14 g, 72%). Continuing elution with heptane/tetrahydrofuran (9:1) provided (4-(3-methyl-2-thienyl)-4-phenylbut-3-en-1-yl)p-toluenesulphonate (0.21 g, 9%).

E- and Z-N-(4-(3-methyl-2-thienyl)-4-phenylbut-3-en-1-yl)nipecotic acid ethyl esters 1-chloro-4-(3-methyl-2-thienyl)-4-phenylbut-3-ene obtained above (0.53 g, 0.002 mole), ethyl nipecotate (0.39 g, 0.0025 mole), potassium carbonate (0.35 g, 0.0025 mole) and potassium iodide (0.42 g, 0.0025 mole) in acetone were stirred at room temperature for 24 h, and at reflux for 40 h. The reaction mixture was cooled, filtered, and the filtrate was evaporated to a residue which was purified by short-path chromatography on silica gel (Art 7729). Elution with ethyl acetate/cyclohexane (1:5) provided the E-ester (0.29 g, 37%) (as confirmed by NMR), some mixed fractions (0.16 g, 21%) and the pure Z-ester (0.06 g, 8%).

E-N-(4-(3-methyl-2-thienyl)-4-phenylbut-3-en-1-yl)nipecotic acid hydrochloride (NO-05-0464)

E-N-(4-(3-methyl-2-thienyl)-4-phenylbut-3-en-1-yl)nipecotic acid ethyl ester obtained above (0.33 g, 0.0086 mole) was saponified under basic conditions similar to those described in Example 1 to give the title acid hydrochloride (0.35 g, 90%) as an amorphous glass (TLC rf 0.49, SiO$_2$/MeOH).

EXAMPLE 12

Z-N-(4-(3-methyl-2-thienyl)-4-phenylbut-3-en-1-yl)nipecotic acid hydrochloride (NO-05-0465)

Z-N-(4-(3-methyl-2-thienyl)-4-phenylbut-3-en-1-yl)nipecotic acid ethyl ester obtained in Example 11 was saponified under basic conditions similar to those described in Example 1 to give the title acid hydrochloride in 73% yield. (TLC rf 0.51, SiO$_2$/MeOH).

The compounds of formula I stated in Table 1 below were prepared similar to the methods described in Examples 1–12. All compounds in Table 1 were isolated as hydrochlorides, except in Examples 54, 58 and 59.

TABLE 1

$$R^1-C(R^2)=CH-CH_2-CH_2-R^3 \quad (I)$$

| Ex. | Isomer | R$^1$ | R$^2$ | R$^3$ | Method | M.p. °C. |
|---|---|---|---|---|---|---|
| 13 | E/Z | phenyl | N-methylpyrrol-2-yl | S-NIP | 1A | 105–7$^1$ |
| 14 | E/Z | 2-methylphenyl | N-(n-propyl)pyrrol-2-yl | R-NIP | 9 | 65–9$^1$ |
| 15 | E/Z | 2-methylphenyl | 3-methylthien-2-yl | GUV | 7 | 212–4$^2$ |
| 16 | E/Z | 4-chloro-2-methylphenyl | 3-methylthien-2-yl | R-MIP | 7 | 207–10$^2$ |
| 17 | E/Z | 2-ethylphenyl | 3-methylthien-2-yl | R-NIP | 7 | 183–4$^2$ |
| 18 | E/Z | 3-methoxyphenyl | 3-methylthien-2-yl | R-NIP | 7 | 60–5$^1$ |
| 19 | E or Z | 4-chlorophenyl | 3-methylthien-2-yl | R-NIP | 7 | 210–2$^2$ |
| 20 | E or Z | 4-chlorophenyl | 3-methylthien-2-yl | GUV | 7 | 218–20$^2$ |
| 21 | E or Z | 4-chlorophenyl | 3-methylthien-2-yl | GUV | 7 | 185–90$^2$ |
| 22 | E/Z | 3-chlorophenyl | 3-methylthien-2-yl | R-NIP | 7 | 100–110$^2$ |
| 23 | E/Z | 4-chloro-2-methylphenyl | 3-methylthien-2-yl | GUV | 10 | 260–4$^2$ |
| 24 | E/Z | 2-fluorophenyl | 3-methylthien-2-yl | R-NIP | 10 | 120–30$^2$ |
| 25 | E/Z | 2-fluorophenyl | 3-methylthien-2-yl | GUV | 10 | 160–70$^2$ |
| 26 | E/Z | 3,5-dimethoxyphenyl | 3-methylthien-2-yl | R-NIP | 7 | 127$^2$ |
| 27 | E/Z | 2,3-dimethoxyphenyl | 3-methylthien-2-yl | GUV | 7 | 15.6, 17.2* |
| 28 | E/Z | 2,3-dimethoxyphenyl | 3-methylthien-2-yl | R-NIP | 7 | 16.5, 18.0* |
| 29 | E or Z | 4-chlorophenyl | 3-methylthien-2-yl | R-NIP | 7 | 160–5$^2$ |
| 30 | E or Z | 2-bromophenyl | 3-methylthien-2-yl | GUV | 7 | 230–1$^2$ |
| 31 | E or Z | 2-bromophenyl | 3-methylthien-2-yl | R-NIP | 7 | 208–10$^2$ |
| 32 | E or Z | 2,6-dimethylphenyl | 3-methylthien-2-yl | R-NIP | 7 | 188–90$^2$ |
| 33 | E/Z | 3-chlorophenyl | 3-methylthien-2-yl | R-NIP | 7 | 175–8$^2$ |
| 34 | E/Z | 2,5-dimethoxyphenyl | 3-methylthien-2-yl | R-NIP | 7 | 65–70$^2$ |
| 35 | E/Z | 2,5-dimethoxyphenyl | 3-methylthien-2-yl | GUV | 7 | 65–70$^2$ |
| 36 | E/Z | 3,5-dichlorophenyl | 3-methylthien-2-yl | GUV | 7 | 105–115$^2$ |
| 37 | E or Z | 3,4-dichlorophenyl | 3-methylthien-2-yl | R-NIP | 7 | 80–110$^1$ |
| 38 | E or Z | 3,4-dichlorophenyl | 3-methylthien-2-yl | GUV | 7 | 242–4$^2$ |
| 39 | E or Z | 2,4-dichlorophenyl | 3-methylthien-2-yl | GUV | 7 | 252–4$^2$ |
| 40 | E or Z | 2,4-dichlorophenyl | 3-methylthien-2-yl | R-NIP | 7 | 196–8$^2$ |
| 41 | E/Z | 2-methoxyphenyl | 3-methylthien-2-yl | R-NIP | 7 | 175–6$^2$ |
| 42 | E/Z | 2-methoxyphenyl | 3-methylthien-2-yl | GUV | 7 | 190–3$^2$ |
| 43 | E/Z | 3-methoxyphenyl | 3-methylthien-2-yl | GUV | 7 | 115–20$^2$ |
| 44 | E/Z | 3,5-dimethoxyphenyl | 3-methylthien-2-yl | GUV | 7 | 97$^2$ |
| 45 | E or Z | 2,6-dimethylphenyl | 3-methylthien-2-yl | GUV | 7 | 98–108$^2$ |
| 46 | E/Z | 2-methylphenyl | 3-methylthien-2-yl | S-NIP | 7 | 196–7$^2$ |
| 47 | E/Z | 4-fluoro-2-methylphenyl | 3-methylthien-2-yl | R-NIP | 10 | 182–4$^2$ |
| 48 | E/Z | 3-chloro-2-methylphenyl | 3-methylthien-2-yl | GUV | 10 | 200–2$^2$ |
| 49 | E/Z | 3-chloro-2-methylphenyl | 3-methylthien-2-yl | R-NIP | 10 | 189–91$^2$ |
| 50 | E or Z | 3,4-dimethoxyphenyl | 3-methylthien-2-yl | R-NIP | 10 | 208–9$^2$ |
| 51 | E or Z | 3,4-dimethoxyphenyl | 3-methylthien-2-yl | GUV | 10 | 230–2$^2$ |
| 52 | E/Z | 2,4-dimethylphenyl | 3-methylthien-2-yl | GUV | 10 | 237 dec.$^2$ |
| 53 | E or Z | phenyl | 3-methylthien-2-yl | GUV | 11 | 0.56** |
| 54 | E/Z | phenyl | N-methylpyrrol-2-yl | R/S-β-homoproline | 1A | 0.88** |
| 55 | E or Z | 4-fluorophenyl | N-methylpyrrol-2-yl | R/S-NIP | 9 | 15.4, 17.8* |
| 56 | E or Z | 2-methylphenyl | N-methylpyrrol-2-yl | GUV | 9 | 102–4$^2$ |
| 57 | E/Z | 4-chloro-2-methylphenyl | N-methylpyrrol-2-yl | R-NIP | 1B | 22.9, 24.3* |
| 58 | E/Z | 2-methylphenyl | N-ethylpyrrol-2-yl | R-NIP | 9 | 19.6, 21.3* |
| 59 | E/Z | phenyl | N-ethylpyrrol-2-yl | GUV | 9 | 15.0, 16.3* |

TABLE 1-continued $$R^1-\underset{\underset{R^2}{|}}{C}=CH-CH_2-CH_2-R^3 \quad (I)$$

| Ex. | Isomer | $R^1$ | $R^2$ | $R^3$ | Method | M.p. °C. |
|---|---|---|---|---|---|---|
| 60 | E/Z | 2-methylphenyl | 5-chloro-3-methylthien-2-yl | R-NIP | 10 | 70–80[2] |

*Retention times in minutes, measured on a 5 μm C-18 (4.6 mm × 250 mm) nucleosil column, eluted with a 20–70% gradient of acetonitrile/0.045 M ammonium acetate pH 4.5 within 30 min.

**Thin layer chromatography retention values measured on silica gel plates, Merck Art. 5714, in methanol

[1]Freeze-dried

[2]Crystallized from acetone, acetone/iPrOH, diethylether or dichloromethane

NIP is Nipecotic acid

GUV is Guvacine

EXAMPLE 61

| Preparation of Capsules Ingredients | Mg per capsule |
|---|---|
| N-(4-(N-methylpyrrol-2-yl)-4-phenylbut-3-en-1-yl)nipecotic acid | 125 |
| Magnesium stearate | 2 |
| Lactose | 200 |

The above ingredients are thoroughly mixed and placed into hard gelatin capsules. Such capsules are administered orally to subjects in need of treatment from 1–5 times daily to enhance GABA'ergic activity in the central nervous system.

EXAMPLE 62

| Preparation of Tablets Ingredients | Mg per Tablet |
|---|---|
| N-(4-(N-methylpyrrol-2-yl)-4-phenylbut-3-en-1-yl)nipecotic acid | 200 |
| Corn starch | 46 |
| Polyvinyl pyrrolidone | 12 |
| Magnesium stearate | 1 |

The compound is thoroughly mixed with two thirds of the corn starch and granulated. The granules obtained are dried, mixed with the remaining ingredients and compressed into tablets. The capsules or tablets thus prepared are administered orally. Similarly, other compounds of formula I can be used.

PHARMACOLOGICAL TEST

Introduction

The convulsions induced by loud noise in the DBA/2 strain of mice is regarded as a reliable model for evaluating anti-epileptic drug effects, cf. E. N. Petersen et al.: Psychopharmacol. 83 (1984), 240, and A. G. Chapman et al.: Arzmeim.Forsch. 10 (1984), 1261. The Rotarod and Traction tests were used to evaluate the sedative properties of the test drugs.

Methods

Male DBA/2 mice (8±1 g) were used in all experiments. The animals were pretrained on the Rotarod (6 rpm; rod diameter 2.5 cm) for 1 min. The compounds tested were injected intra-peritoneally. Twenty-five min, later the animals underwent a 2 min. test on the Rotarod. The number of failures to stay on the rod was counted. An error rate higher than 10 was assigned the maximum score of 10. Immediately after the Rotarod test, the animals were tested in a Traction test, cf. Psychopharmacol. above. In this test, the animal was required to maintain grasp on a thin rod (diameter 2.5 mm) with the forepaws for five sec. and, within this period of time, to show a traction response (grasping onto the rod with one of the hindlegs). The performance on the test was based on the absence or presence of the traction response with the 5 sec. test period. Finally, after the Traction test, the animals were individually placed in a chamber in which they were exposed for 30 sec. to a 14 kHz sinus tone at 111 dB. During this period of time, the following behaviours were noted: "wild running", clonic convulsions and death.

Drugs

The compounds tested were dissolved in distilled water or suspended in 5% chremophore. The injection volume was 0.2 ml/mouse.

Results obtained

In table 2, below, the ratio $ED_{50}$ Rotarod/$ED_{50}$ tonic convulsions is given for the compounds tested. NO-05-0340 is R-N-(4-(2-methylphenyl)-4-(3-methyl-2-thienyl)but-3-en-1-yl)nipecotic acid and NO-05-0356 is R-N-(4-(N-methylpyrrol-2-yl)-4-phenylbut-3-en-1-yl)nipecotic acid.

TABLE 2

| Compound | Ratio |
|---|---|
| NO-05-0340 | 8 |
| NO-05-0356 | 21 |
| SK&F 100220A | 1 |
| SK&F 89976A | 5 |
| SK&F 100561 | 7 |

In Vitro Test

GABA-uptake inhibition was measured essentially as described by Fjalland (Acta Pharmacol. et. Toxicol. (1978), 42, 73–76) using 25 mM of 3H-GABA as a substrate. The results obtained appear from Table 3, the obtained values being from two separate experiments using 3–5 different concentrations of test compound.

TABLE 3

$$R^1-\underset{\underset{R^2}{|}}{C}=CH-CH_2-CH_2-R^3 \quad (I)$$

| $R^1$ | $R^2$ | $R^3$ | Isomer | $IC_{50}$ (nM) |
|---|---|---|---|---|
| phenyl | N-methylpyrrol-2-yl | guvacine | —;(E/Z) | 126 |
| phenyl | N-methylpyrrol-2-yl | nipecotic acid | R;(E/Z) | 68 |
| 2-methylphenyl | 3-methylthien-2-yl | nipecotic acid | R;(E/Z) | 74 |
| 3-methoxyphenyl | 3-methylthien-2-yl | nipecotic acid | R;(E/Z) | 56 |
| 2-methylphenyl | N-n-propylpyrrol-2-yl | nipecotic acid | R;(E/Z) | 85 |
| 4-chloro-2-methylphenyl | N-methylpyrrol-2-yl | nipecotic acid | R;(E/Z) | 148 |
| 3-chlorophenyl | 3-methylthien-2-yl | nipecotic acid | R;(E/Z) | 124 |
| 2-methylphenyl | 3-methylthien-2-yl | guvacine | —;(E/Z) | 117 |
| 3-ethylphenyl | 3-methylthien-2-yl | nipecotic acid | R;(E/Z) | 72 |
| 4-chloro-2-methylphenyl | 3-methylthien-2-yl | nipecotic acid | R;(E/Z) | 89 |
| 2-fluorophenyl | 3-methylthien-2-yl | nipecotic acid | R;(E/Z) | 217 |
| 3-chloro-2-methylphenyl | 3-methylthien-2-yl | nipecotic acid | R;(E/Z) | 104 |
| 2,4-dimethylphenyl | 3-methylthien-2-yl | nipecotic acid | R;(E/Z) | 190 |
| phenyl | N-ethylpyrrol-2-yl | guvacine | —;(E/Z) | 162 |
| 2-methylphenyl | N-ethylpyrrol-2-yl | nipecotic acid | R;(E/Z) | 49 |
| phenyl | thien-2-yl (U.S. Pat. No. 4.383.999 example 18) | nipecotic acid | R/S;(E/Z) | 470 |
| phenyl | thien-2-yl (not disclosed in U.S. Pat. No. 4.383.999) | nipecotic acid | R;(E/Z) | 236 |
| phenyl | thien-2-yl (not disclosed in U.S. Pat. No. 4.383.999) | guvacine | —;(E/Z) | 217 |

It is readily apparent from the above Table 3 that the novel compounds of the present invention provides compounds which are by far superior over the considered closest prior art compounds, as well as over obvious modifications of such prior art compounds.

It is readily apparent from the above Table 3 that the novel compounds of the present invention provides compounds which are by far superior over the considered closest prior art compounds, as well as over obvious modifications of such prior art compounds.

I claim:

1. Phenylbuten of the formula I

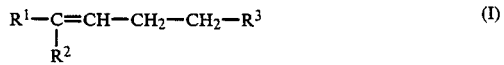

wherein $R^1$ represents phenyl, or phenyl substituted by one, or more substituents selected from the group consisting of halogen, $C_{1-7}$-alkyl, and $C_{1-7}$-alkoxy, $R^2$ represents furanyl, thienyl, pyridyl or pyrrolyl ortho substituted with $C_{1-7}$-alkyl or halogen and wherein $R^3$ represents 3-carboxypiperidin-1-yl, 3-carboxy-1,2,5,6-tetrahydropyridin-1-yl or 3-carboxymethyl-pyrrolidin-1-yl.

2. A compound, according to claim 1, characterized in that $R^3$ is 3-carboxypiperidin-1-yl, or 3-carboxy-1,2,5,6-tetrahydropyridin-1-yl.

3. A compound, according to claim 1, characterized in that $R^2$ represents pyrrolyl, furanyl, or thienyl each of which is substituted with $C_{1-6}$-alkyl ortho to the radical position.

4. Compounds of claim 1 wherein $R^1$ is 2-methylphenyl, $R^2$ is 3-methylthien-2-yl and $R^3$ is guvacine or nipecotic acid.

5. Compound of claim 1 wherein $R^1$ is 4-chloro-2-methylphenyl, $R^2$ is 3-methylthien-2-yl and $R^3$ is nipecotic acid.

6. Compound of claim 1 wherein $R^1$ is 2-ethylphenyl, $R^2$ is 3-methylthien-2-yl and $R^3$ is nipecotic acid.

7. Compound of claim 1 wherein $R^1$ is 3-chlorophenyl, 3-methylthien-2-yl and $R^3$ is nipecotic acid.

8. Compound of claim 1 wherein $R^1$ is 3-methoxyphenyl, $R^2$ is 3-methylthien-2-yl and $R^3$ is nipecotic acid.

9. Compound of claim 1 wherein $R^1$ is phenyl, $R^2$ is N-methylpyrrol-2-yl and $R^3$ is nipecotic acid or guvacine.

10. Compound of claim 1 wherein $R^1$ is 2-methylphenyl, $R^2$ is N-methylpyrrol-2-yl and $R^3$ is nipecotic acid or guvacine.

11. A compound selected from the group consisting of:
N-(4-(N-Methylpyrrol-2-yl)-4-phenylbut-3-enyl)guvacine,
N-(4-(N-Methylpyrrol-2-yl)-4-phenylbut-3-enyl)nipecotic acid,
N-(4-(N-Methylpyrrol-2-yl)-4-phenylbut-3-enyl)-β-homoproline,
N-(4-(2-Methylphenyl)-4-(N-methylpyrrol-2-yl)but-3-enyl)guvacine,
N-(4-(2-Methylphenyl)-4-(N-methylpyrrol-2-yl)but-3-enyl)nipecotic acid,
N-(4-(2-Methylphenyl)-4-(N-methylpyrrol-2-yl)but-3-enyl)-β-homoproline,
N-(4-(3-Methylthien-2-yl)-4-phenylbut-3-enyl)guvacine,
N-(4-(3-Methylthien-2-yl)-4-phenylbut-3-enyl)nipecotic acid,
N-(4-(3-Methylthien-2-yl)-4-phenylbut-3-enyl)-β-homoproline,
N-(4-(2-Methylphenyl)-4-(N-ethylpyrrol-2-yl)but-3-enyl)guvacine,
N-(4-(2-Methylphenyl)-4-(N-ethylpyrrol-2-yl)but-3-enyl)nipecotic acid,
N-(4-(2-Methylphenyl)-4-(N-ethylpyrrol-2-yl)but-3-enyl)-β-homoproline,
N-(4-(2-Methylphenyl)-4-(N-npropylpyrrol-2-yl)but-3-enyl)guvacine,
N-(4-(2-Methylphenyl)-4-(N-npropylpyrrol-2-yl)but-3-enyl)nipecotic acid,
N-(4-(2-Methylphenyl)-4-(N-npropylpyrrol-2-yl)but-3-enyl)-β-homoproline, N-(4-(2-Ethylphenyl)-4-(N-methylpyrrol-2-yl)but-3-enyl)guvacine,
N-(4-(2-Ethylphenyl)-4-(N-methylpyrrol-2-yl)but-3-enyl)nipecotic acid,
N-(4-(2-Ethylphenyl)-4-(N-methylpyrrol-2-yl)but-3-enyl)-β-homoproline,
N-(4-(2-Methylphenyl)-4-(3-methylthien-2-yl)but-3-enyl)guvacine,
N-(4-(2-Methylphenyl)-4-(3-methylthien-2-yl)but-3-enyl)nipecotic acid,
N-(4-(2-Methylphenyl)-4-(3-methylthien-2-yl)but-3-enyl)-β-homoproline,
N-(4-(2-Ethylphenyl)-4-(3-methylthien-2-yl)but-3-enyl)guvacine,
N-(4-(2-Ethylphenyl)-4-(3-methylthien-2-yl)but-3-enyl)nipecotic acid,
N-(4-(2-Ethylphenyl)-4-(3-methylthien-2-yl)but-3-enyl)-β-homoproline,
N-(4-(2-Ethylphenyl)-4-(3-ethylthien-2-yl)but-3-enyl)-guvacine,
N-(4-(2-Ethylphenyl)-4-(3-ethylthien-2-yl)but-3-enyl)-nipecotic acid,
N-(4-(2-Ethylphenyl)-4-(3-ethylthien-2-yl)but-3-enyl)-β-homoproline,
N-(4-(N-Ethylpyrrol-2-yl)-4-phenylbut-3-enyl)guvacine,
N-(4-(N-Ethylpyrrol-2-yl)-4-phenylbut-3-enyl)nipecotic acid,
N-(4-(N-Ethylpyrrol-2-yl)-4-phenylbut-3-enyl)-β-homoproline,
N-(4-(4-Fluorophenyl)-4-(N-methylpyrrol-2-yl)but-3-enyl)guvacine,
N-(4-(4-Fluorophenyl)-4-(N-methylpyrrol-2-yl)but-3-enyl)nipecotic acid,
N-(4-(4-Fluorophenyl)-4-(N-methylpyrrol-2-yl)but-3-enyl)-β-homoproline,
N-(4-(3-Methylfuran-2-yl)-4-(2-methylphenyl)but-3-enyl)guvacine,
N-(4-(3-Methylfuran-2-yl)-4-(2-methylphenyl)but-3-enyl)nipecotic acid,
N-(4-(3-Methylfuran-2-yl)-4-(2-methylphenyl)but-3-enyl)-β-homoproline,
N-(4-(2,4-Dimethylphenyl)-4-(3-methylthien-2-yl)but-3-enyl)guvacine,
N-(4-(2,4-Dimethylphenyl)-4-(3-methylthien-2-yl)but-3-enyl)nipecotic acid,
N-(4-(2,4-Dimethylphenyl)-4-(3-methylthien-2-yl)but-3-enyl)-β-homoproline,
N-(4-(4-Chloro-2-methylphenyl)-4-(N-methylpyrrol-2-yl)but-3-enyl)guvacine,
N-(4-(4-Chloro-2-methylphenyl)-4-(N-methylpyrrol-2-yl)but-3-enyl)nipecotic acid,
N-(4-(4-Chloro-2-methylphenyl)-4-(N-methylpyrrol-2-yl)but-3-enyl)-β-homoproline,
N-(4-(4-Chloro-2-methylphenyl)-4-(3-methylthien-2-yl)but-3-enyl)guvacine,
N-(4-(4-Chloro-2-methylphenyl)-4-(3-methylthien-2-yl)but-3-enyl)nipecotic acid,
N-(4-(4-Chloro-2-methylphenyl)-4-(3-methylthien-2-yl)but-3-enyl)-β-homoproline,
N-(4-(2-Fluorophenyl)-4-(3-methylthien-2-yl)but-3-enyl)guvacine,
N-(4-(2-Fluorophenyl)-4-(3-methylthien-2-yl)but-3-enyl)nipecotic acid,
N-(4-(2-Fluorophenyl)-4-(3-methylthien-2-yl)but-3-enyl)-β-homoproline,
N-(4-(2,3-Dimethoxyphenyl)-4-(3-methylthien-2-yl)but-3-enyl)guvacine,
N-(4-(2,3-Dimethoxyphenyl)-4-(3-methylthien-2-yl)but-3-enyl)nipecotic acid,
N-(4-(2,3-Dimethoxyphenyl)-4-(3-methylthien-2-yl)but-3-enyl)-β-homoproline,
N-(4-(4-Chlorophenyl)-4-(3-methylthien-2-yl)but-3-enyl)guvacine,
N-(4-(4-Chlorophenyl)-4-(3-methylthien-2-yl)but-3-enyl)nipecotic acid,
N-(4-(4-Chlorophenyl)-4-(3-methylthien-2-yl)but-3-enyl)-β-homoproline,
N-(4-(3-Chlorophenyl)-4-(3-methylthien-2-yl)but-3-enyl)guvacine,
N-(4-(3-Chlorophenyl)-4-(3-methylthien-2-yl)but-3-enyl)nipecotic acid,
N-(4-(3-Chlorophenyl)-4-(3-methylthien-2-yl)but-3-enyl)-β-homoproline,
N-(4-(2,5-Dimethoxyphenyl)-4-(3-methylthien-2-yl)but-3-enyl)guvacine,
N-(4-(2,5-Dimethoxyphenyl)-4-(3-methylthien-2-yl)but-3-enyl)nipecotic acid,
N-(4-(2,5-Dimethoxyphenyl)-4-(3-methylthien-2-yl)but-3-enyl)-β-homoproline,
N-(4-(3,5-Dichlorophenyl)-4-(3-methylthien-2-yl)but-3-enyl)guvacine,
N-(4-(3,5-Dichlorophenyl)-4-(3-methylthien-2-yl)but-3-enyl)nipecotic acid,
N-(4-(3,5-Dichlorophenyl)-4-(3-methylthien-2-yl)but-3-enyl)-β-homoproline,
N-(4-(3,4-Dichlorophenyl)-4-(3-methylthien-2-yl)but-3-enyl)guvacine,
N-(4-(3,4-Dichlorophenyl)-4-(3-methylthien-2-yl)but-3-enyl)nipecotic acid,
N-(4-(3,4-Dichlorophenyl)-4-(3-methylthien-2-yl)but-3-enyl)-β-homoproline,
N-(4-(2,4-Dichlorophenyl)-4-(3-methylthien-2-yl)but-3-enyl)guvacine,
N-(4-(2,4-Dichlorophenyl)-4-(3-methylthien-2-yl)but-3-enyl)nipecotic acid,
N-(4-(2,4-Dichlorophenyl)-4-(3-methylthien-2-yl)but-3-enyl)-β-homoproline,
N-(4-(2-Methoxyphenyl)-4-(3-methylthien-2-yl)but-3-enyl)guvacine,
N-(4-(2-Methoxyphenyl)-4-(3-methylthien-2-yl)but-3-enyl)nipecotic acid,
N-(4-(2-Methoxyphenyl)-4-(3-methylthien-2-yl)but-3-enyl)-β-homoproline,
N-(4-(3-Methoxyphenyl)-4-(3-methylthien-2-yl)but-3-enyl)guvacine,
N-(4-(3-Methoxyphenyl)-4-(3-methylthien-2-yl)but-3-enyl)nipecotic acid,
N-(4-(3-Methoxyphenyl)-4-(3-methylthien-2-yl)but-3-enyl)-β-homoproline,
N-(4-(3,5-Dimethoxyphenyl)-4-(3-methylthien-2-yl)but-3-enyl)guvacine,
N-(4-(3,5-Dimethoxyphenyl)-4-(3-methylthien-2-yl)but-3-enyl)nipecotic acid,
N-(4-(3,5-Dimethoxyphenyl)-4-(3-methylthien-2-yl)but-3-enyl)-β-homoproline,
N-(4-(2,6-Dimethylphenyl)-4-(3-methylthien-2-yl)but-3-enyl)guvacine,
N-(4-(2,6-Dimethylphenyl)-4-(3-methylthien-2-yl)but-3-enyl)nipecotic acid,
N-(4-(2,6-Dimethylphenyl)-4-(3-methylthien-2-yl)but-3-enyl)-β-homoproline,
N-(4-(4-Fluoro-2-methylphenyl)-4-(3-methylthien-2-yl)but-3-enyl)guvacine,
N-(4-(4-Fluoro-2-methylphenyl)-4-(3-methylthien-2-yl)but-3-enyl)nipecotic acid, N-(4-(4-Fluoro-2-methylphenyl)-4-(3-methylthien-2-yl)but-3-enyl)-β-homoproline,
N-(4-(3-Chloro-2-methylphenyl)-4-(3-methylthien-2-yl)but-3-enyl)guvacine,
N-(4-(3-Chloro-2-methylphenyl)-4-(3-methylthien-2-yl)but-3-enyl)nipecotic acid,
N-(4-(3-Chloro-2-methylphenyl)-4-(3-methylthien-2-yl)but-3-enyl)-β-homoproline,
N-(4-(3,4-Dimethoxyphenyl)-4-(3-methylthien-2-yl)but-3-enyl)guvacine,
N-(4-(3,4-Dimethoxyphenyl)-4-(3-methylthien-2-yl)but-3-enyl)nipecotic acid,
N-(4-(3,4-Dimethoxyphenyl)-4-(3-methylthien-2-yl)but-3-enyl)-β-homoproline,
N-(4-(3-Chlorothien-2-yl)-4-(2-methylphenyl)but-3-enyl)guvacine,
N-(4-(3-Chlorothien-2-yl)-4-(2-methylphenyl)but-3-enyl)nipecotic acid,
N-(4-(3-Chlorothien-2-yl)-4-(2-methylphenyl)but-3-enyl)-β-homoproline,
N-(4-(3-Bromothien-2-yl)-4-(2-methylphenyl)but-3-enyl)guvacine,
N-(4-(3-Bromothien-2-yl)-4-(2-methylphenyl)but-3-enyl)nipecotic acid,
N-(4-(3-Bromothien-2-yl)-4-(2-methylphenyl)but-3-enyl)-β-homoproline,
N-(4-(3-Chlorothien-2-yl)-4-phenylbut-3-enyl)guvacine,
N-(4-(3-Chlorothien-2-yl)-4-phenylbut-3-enyl)nipecotic acid,
N-(4-(3-Chlorothien-2-yl)-4-phenylbut-3-enyl)-β-homoproline,
N-(4-(3-Bromothien-2-yl)-4-phenylbut-3-enyl)guvacine,
N-(4-(3-Bromothien-2-yl)-4-phenylbut-3-enyl)nipecotic acid,
N-(4-(3-Bromothien-2-yl)-4-phenylbut-3-enyl)-β-homoproline.

12. Pharmaceutical compositions containing a carrier and an effective amount of a compound of formula I

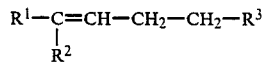

wherein $R^1$ represents phenyl, or phenyl substituted by one, or more substituents selected from the group consisting of halogen, $C_{1-7}$-alkyl, and $C_{1-7}$-alkoxy, $R^2$ represents furanyl, thienyl, pyridyl or pyrrolyl ortho substituted with $C_{1-7}$-alkyl or halogen and wherein $R^3$ represents 3-carboxypiperidin-1-yl, 3-carboxy-1,2,5,6-tetrahydropyridinyl-1-yl or 3-carboxymethyl-pyrrolidin-1-yl or a salt thereof.

13. Compositions, according to claim 12, characterized in that they contain from about 25 mg to about 1 g of the compound.

14. A method of treating a central nervous system ailment in a subject in need of such treatment comprising the step of administering to said subject an amount of a compound of the below stated formula I which is effective for the alleviation of such ailment

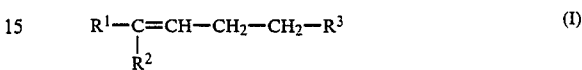

wherein $R^1$ represents phenyl, or phenyl substituted by one, or more substituents selected from the group consisting of halogen, $C_{1-7}$-alkyl, and $C_{1-7}$-alkoxy, $R^2$ represents furanyl, thienyl, pyridyl or pyrrolyl ortho substituted with $C_{1-7}$-alkyl or halogen and wherein $R^3$ represents 3-carboxypiperidin-1-yl, 3-carboxy-1,2,5,6-tetrahydropyridin-1-yl or 3-carboxymethyl-pyrrolidin-1-yl.

15. A method of treating a central nervous system ailment in a subject in need of such treatment comprising the step of administering to said subject an amount of a compound of the below stated formula I which is effective for the alleviation of such ailment in the form of a pharmaceutical composition thereof, in which (it) the compound of formula I is present together with a pharmaceutically acceptable carrier or diluent

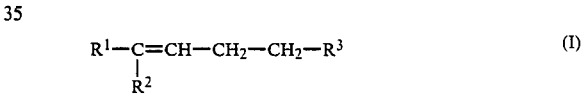

wherein $R^1$ represents phenyl, or phenyl substituted by one, or more substituents selected from the group consisting of halogen, $C_{1-7}$-alkyl, and $C_{1-7}$-alkoxy, $R^2$ represents furanyl, thienyl, pyridyl or pyrrolyl ortho substituted with $C_{1-7}$-alkyl or halogen and wherein $R^3$ represents 3-carboxypiperidin-1-yl, 3-carboxy-1,2,5,6-tetrahydropyridin-1-yl or 3-carboxymethyl-pyrrolidin-1-yl.

* * * * *